(12) United States Patent
Gallant et al.

(10) Patent No.: US 6,325,097 B1
(45) Date of Patent: *Dec. 4, 2001

(54) MANIFOLD AND REGULATOR APPARATUS (75) Inventors: Dennis J. Gallant, Harrison, OH (US);
John W. Ruehl, Shelbyville, IN (US);
John C. Gray, Huntsville, AL (US);
Edward W. Catton, New Palestine;
Jerome B. Batta, Guilford, both of IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/318,125

(22) Filed: May 25, 1999

Related U.S. Application Data (63) Continuation-in-part of application No. 08/792,881, filed on Jan. 31, 1997, now Pat. No. 5,966,760.

(51) Int. Cl.⁷ .................................................. G05D 16/04
(52) U.S. Cl. ........................... 137/505; 137/507; 137/884
(58) Field of Search ...................................... 137/507, 510, 137/884, 505

(56) References Cited

U.S. PATENT DOCUMENTS

| | | |
|---|---|---|
| 3,026,079 | 3/1962 | Stack . |
| 4,003,584 * | 1/1977 | Zelli . |
| 4,174,733 * | 11/1979 | Eidsmore et al. .............. 137/884 X |
| 4,417,648 | 11/1983 | Anderson et al. . |
| 4,494,572 | 1/1985 | Loveless . |
| 4,547,092 | 10/1985 | Vetter et al. . |
| 4,646,211 | 2/1987 | Gallant et al. . |
| 4,672,728 | 6/1987 | Nimberger . |
| 4,790,610 | 12/1988 | Welch et al. . |
| 4,821,470 | 4/1989 | Kappers et al. . |
| 5,060,425 | 10/1991 | Kappers et al. . |
| 5,072,906 | 12/1991 | Foster . |
| 5,117,521 | 6/1992 | Foster et al. . |
| 5,186,337 | 2/1993 | Foster et al. . |
| 5,284,255 | 2/1994 | Foster et al. . |
| 5,299,773 | 4/1994 | Bertrand . |

(List continued on next page.)

FOREIGN PATENT DOCUMENTS

| | | | |
|---|---|---|---|
| 2 018 094 | * | 12/1990 | (CA) . |
| 298 05 019 | * | 6/1998 | (DE) . |
| 298 20 372 U 1 | | 4/1999 | (DE) . |
| 0 400 407 | * | 12/1990 | (EP) . |
| 2 669 199 | * | 5/1992 | (FR) . |
| 98/33419 | | 8/1998 | (WO) . |

OTHER PUBLICATIONS

"Lettuce Trade Your Spaghetti for TheCABG Cart", CABG Cart advertising brochure, 5 pages, date unknown.
"Stabilet From Hill–Rom", Hill–Rom product brochure, 6 pages, 1992.

Primary Examiner—Stephen M. Hepperle
(74) Attorney, Agent, or Firm—Barnes & Thornburg (57) ABSTRACT

A manifold assembly is provided which includes a manifold block having a gas inlet and a gas outlet. The block also includes a regulator inlet in a planar surface of the manifold block which is connected to the gas inlet. The regulator outlet is also provided in the planar surface spaced from the regulator inlet and connected to the gas outlet. A regulator is mounted to the manifold block at the planar surface and includes an inlet and outlet on a common wall of the regulator. The inlet and outlet of the regulator have the same spacing as and communicates with the regulator inlet and outlet of the manifold block. In the preferred embodiment, one of the inlet and outlet of the regulator is annular and encompasses the other.

50 Claims, 8 Drawing Sheets

U.S. PATENT DOCUMENTS

| | | |
|---|---|---|
| 5,323,565 | 6/1994 | Kappers et al. . |
| 5,335,651 | 8/1994 | Foster et al. . |
| 5,337,845 | 8/1994 | Foster et al. . |
| 5,344,169 * | 9/1994 | Pryor et al. . |
| 5,370,111 | 12/1994 | Reeder et al. . |
| 5,377,371 | 1/1995 | Foster . |
| 5,398,359 | 3/1995 | Foster . |
| 5,457,831 | 10/1995 | Foster et al. . |
| 5,492,146 * | 2/1996 | George et al. .................... 137/510 X |
| 5,497,766 * | 3/1996 | Foster et al. . |
| 5,562,091 | 10/1996 | Foster et al. . |
| 5,567,885 | 10/1996 | Garside . |
| 5,598,869 | 2/1997 | Nelson . |
| 5,602,345 | 2/1997 | Wenger et al. . |
| 5,681,116 | 10/1997 | Lin . |
| 5,711,340 | 1/1998 | Gusky et al. . |
| 5,720,317 | 2/1998 | Nimberger . |
| 5,725,024 | 3/1998 | Nimberger . |
| 5,836,355 * | 11/1998 | Markulec et al. ................... 137/884 |
| 6,003,555 | 12/1999 | Sheng . |

* cited by examiner

MANIFOLD AND REGULATOR APPARATUS

CROSS-REFERENCE

This is a continuation-in-part of U.S. patent application Ser. No. 08/792,881 filed Jan. 31, 1997, now U.S. Pat. No. 5,966,760.

BACKGROUND AND SUMMARY OF THE INVENTION

The present invention relates to manifolds and gas regulator apparatus and more specifically, to a manifold and gas regulator apparatus for use in a hospital environment.

Air and oxygen are two common gases which are available in hospital rooms for patient care. They are also required on mobile carts to be used with a bed which is displaced from a wall or pivotal tower unit. A manifold provides the appropriate connections between the gas supply or source and the dispensing apparatus. Also, regulation and monitoring of the gas supply and flow must be provided. Where the regulator must select between a wall source and a portable source of gas, a change over mechanism must be provided on the manifold.

According to one aspect of the invention, a manifold assembly is provided which includes a manifold block having a gas inlet and a gas outlet. The block also includes a regulator inlet in a planar surface of the manifold block which is connected to the gas inlet. The regulator outlet is also provided in the planar surface spaced from the regulator inlet and connected to the gas outlet. A regulator is mounted to the manifold block at the planar surface and includes an inlet and outlet on a common wall of the regulator. The inlet and outlet of the regulator have the same spacing as and communicates with the regulator inlet and outlet of the manifold block.

In the preferred embodiment, one of the inlet and outlet of the regulator is annular and encompasses the other. A first seal encompasses the annual inlet or outlet of the regulator and a second seal is provided between the annular inlet or outlet and the other of the inlet or outlet of the regulator. The first and second seals may be O-rings located within first and second annular notches formed in the end wall of the regulator. In one embodiment, the inlet of the regulator includes a threaded stem coupled to the regulator inlet of the manifold block. In another embodiment, one or more threaded fasteners couple the regulator to the manifold block. In that embodiment, one of the inlet or outlet of the regulator and the one or more fasteners are aligned in a circle which encompass the other of the inlet or outlet. In the second embodiment, the regulator includes a body and a bonnet threadably mounted on the body and the bonnet covers the fasteners.

The manifold block has a top, bottom and side walls. In one embodiment, the planar surfaces is on a side wall of the block. In this embodiment, the gas inlet is on the same side wall as the planar surface. A second gas inlet is provided on the bottom wall. Also, the gas outlet is on the bottom wall. The manifold also includes a second gas outlet on the top wall. In a second embodiment, the planar surface for the regulator is on the bottom wall. In this embodiment, the gas inlet is on the side wall of the block and a second gas inlet is on the bottom wall. A gas outlet is on another side wall. The second gas outlet is on the same wall as the gas inlet.

According to an additional aspect of the present invention, a pressure regulator apparatus is provided for reducing pressure of a gas received from a gas outlet aperture formed in a planar surface and for delivering reduced pressure gas to a gas inlet aperture formed in the planar surface spaced apart from the gas outlet aperture by a first distance. The regulator apparatus includes a regulator body for reducing gas pressure. The body includes an end wall having a regulator inlet configured to be coupled to the gas outlet aperture, a first annular seal located a second distance from the regulator inlet, a second annular seal located a third distance from the regulator inlet, and a regulator outlet formed in the end wall between the first and second seals. The second distance is less than the first distance, and the third distance is greater than the first distance. The first and second seals are configured to engage the planar surface on opposite sides of the gas inlet aperture so that gas from the regulator outlet flows into the gas inlet aperture formed in the planar surface.

In the illustrated apparatus, the end wall is formed to include an annular groove surrounding the regulator inlet. The annular groove is spaced apart from the regulator inlet by the first distance so that the annular groove is aligned with the gas inlet aperture formed in the planar surface when the regulator inlet is coupled to the gas outlet aperture. The regulator outlet is formed in communication with the annular groove.

Also in the illustrated apparatus, the regulator inlet includes a threaded stem configured to be coupled to the gas outlet aperture. The first and second seals are O-ring seals located within first and second annular notches formed in the end wall of the regulator body.

Additional objects, features, and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE PREFERRED EMBODIMENTS

Figure 1:
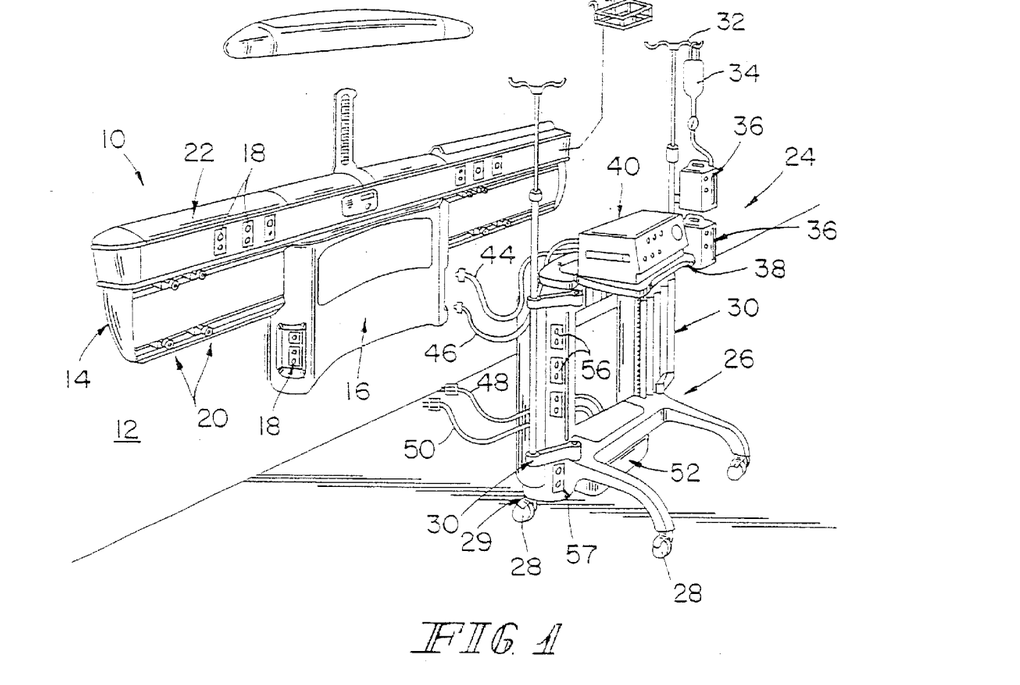
FIG. 1 is a perspective view of the system of the present invention including a headwall mounted on a hospital room wall and a mobile care cart configured to be located adjacent the headwall to upgrade the hospital room to a critical care room.
Figure 2:
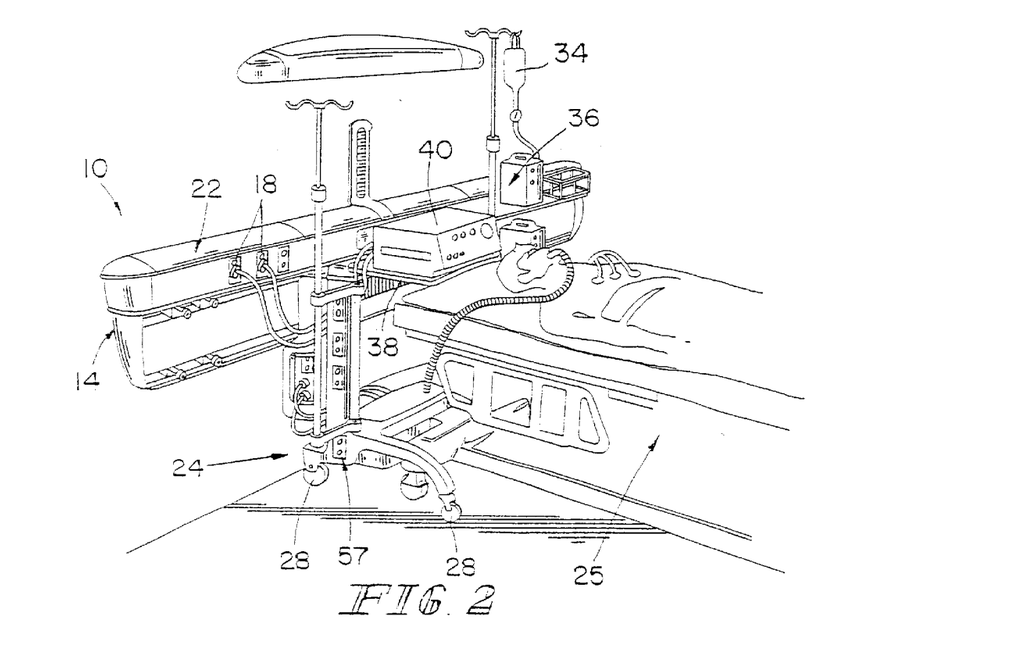
FIG. 2 is a perspective view illustrating the care cart docked or nested with the headwall and with a hospital bed positioned in the room adjacent the care cart to provide critical care services to a patient.

Referring now to the drawings, FIGS. 1 and 2 illustrate a system and structural components in which the present invention may be used by way of example only. As illustrated in FIG. 1, a headwall 10 is mounted on a wall 12 of a hospital room. The headwall 10 includes an elongated body section 14 and a bed locator section 16. The headwall 10 includes outlets 18 for electrical power and outlets 20 for oxygen, air, and vacuum. Preferably, outlets 20 are movable gas outlets. The headwall 10 also includes a foldable concealment cover 22 configured to hide an internal raceway. The headwall 10 can be used by itself in the room to provide for general care and support and for med-surg patients, for example.

When it is desired to upgrade the hospital room into a critical care room, a care cart 24 is moved into the room. The care cart 24 includes a base 26 having casters 28. The rear casters 28 are lockable by separate brakes 29. A pair of pivoting IV poles 30 are mounted on the base 26. The poles 30 include hooks 32 for hanging IV bags 34. IV pumps 36 may also be mounted on the poles 30. Care cart 24 also includes an equipment support shelf 38 for supporting a full end ventilator 40 or other critical care equipment. Ventilator 40 may be secured to the shelf 38 by latching brackets (not shown).

The mobile care cart 24 further includes an air hose 44, an oxygen hose 46, a battery power cord 48, and a standard power cord 50. It is understood that a single cord may be used if desired. Care cart 24 also includes a transport battery 52 to operate equipment during transport of the critical care patient. The battery 52 provides power for the ventilator 40 and other critical care equipment during transport. The IV pumps 36 and transport monitor 42 each typically have an internal power supply. The battery 52 is recharged when the care cart 24 is plugged into the wall outlets 18.

Care cart 24 includes an upper series of electrical outlets 56 which are powered only when the care cart is plugged into the headwall outlet 18. Care cart 24 includes separate power outlets 57 which are automatically powered by the battery 52 when the care cart 24 is unplugged from outlets 18. Therefore, the equipment requiring power during transport must be plugged into the designated lower outlets 57 for an uninterrupted power supply from the battery 52.

In order to upgrade the hospital room to a critical care room, care cart 24 is moved into the position illustrated in FIG. 2. Power cords 48 and 50 are plugged into the outlets 18 of headwall 10. Air and oxygen lines 44 and 46 are connected to the gas outlets 20. In the position of FIG. 2, the battery 52 is recharged and air and oxygen tanks 54 are shut off to keep the tank supplies from being depleted. Also as illustrated in FIG. 2, the care cart 24 is configured to nest with the locator section 16 of headwall 10. Therefore, the hospital room can be upgraded to a critical care room without reconstruction.

The care cart 24 is also used to transport the critical care patient within the hospital. For example, the care cart 24 is coupled to the hospital bed 25. Using the care cart 24 to transport the patient provides seamless care for the patient during transport to the radiology department or other diagnostic testing facility within the hospital.

Figure 3:
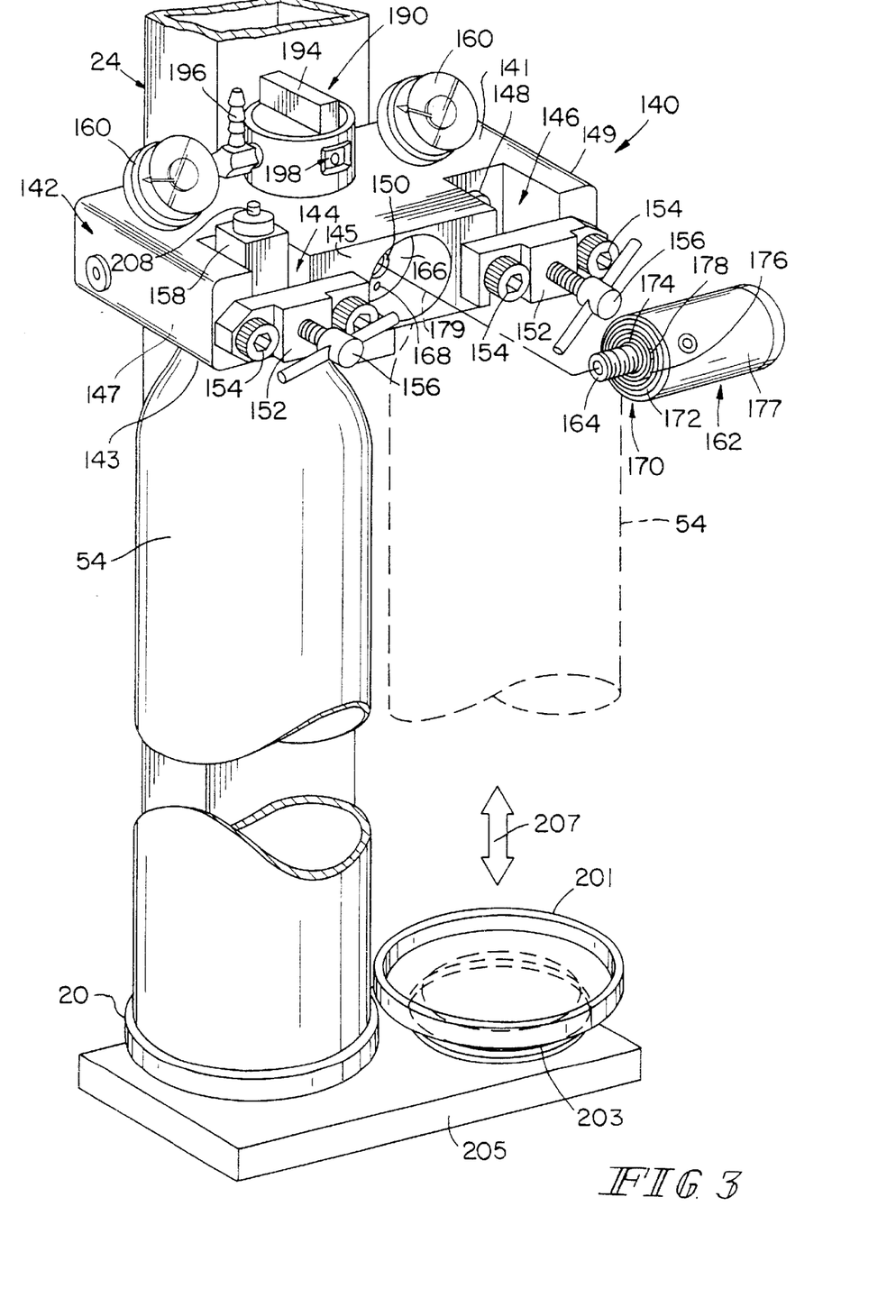
FIG. 3 is a perspective view of a manifold assembly for coupling oxygen or air tanks to the care cart and illustrating a pair of spring-loaded platforms for supporting gas tanks on the care cart.

When it is desired to transport the critical care patient, oxygen and air tanks 54 are loaded on to the care cart 24 as shown in FIG. 3. Prior to transport, valves on the oxygen and air tanks are manually opened to supply gas through the manifold to the ventilator 40. The gas lines 44 and 46 and power cords 48 and 50 of care cart 24 are then disconnected from headwall 10. Battery 52 on care cart 24 automatically switch on to support the ventilator 40 when the power cords 48 and 50 are disconnected.

The IV lines and vent circuits do not need to be disconnected from the patient prior to transport. The IV pumps 36 and ventilator 40 also do not need to be handled. This method maintains seamless, uninterrupted functioning of the life support to the patient.

At the destination, the care cart 24 is coupled to medical gas and wall electrical outlets to prevent depleting of the on-board gas tank 54 supplies and battery 52. A cross over valve 180 allows the cart to be connected to the medical gas supply for a limited period of time with negligible leakage of gas from the tanks 54. The patient can then be transferred to a scanning table. The bed 25 can be removed from the care cart 24 and taken from the room. Therefore, the care cart 24 can remain adjacent the scanning table to continue to provide life support for the patient.

Figure 4:
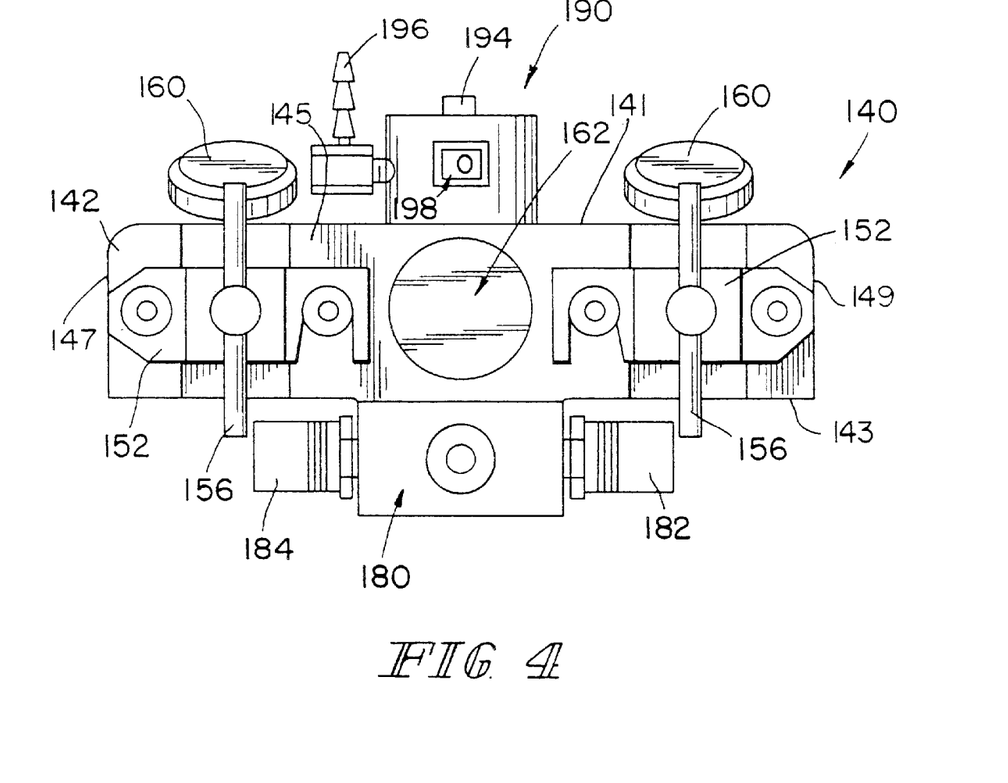
FIG. 4 is a front elevational view of the manifold of FIG. 3.

FIGS. 3 and 4 illustrate further details of one embodiment of a manifold assembly 140. Manifold assembly 140 includes a manifold block 142 coupled to care cart 24. The manifold block 142 includes top wall 141, bottom wall 143, front side wall 145, left side wall 147 and right side wall 149. Manifold block 142 includes first and second recessed sections 144 and 146 for receiving two separate air or oxygen gas tanks 54. A gas inlet 148 is located on front wall 145 in each of recessed sections 144 and 146. Therefore, two gas inlets 148 are provided so that both tanks 54 supply single gas outlet 150 also on front wall 145. Gas inlets 148 are formed by sized threads designed to receive specific gas connections.

Mounting plates 152 and fasteners 154 are used to secure the tanks 54 to the manifold block 142. Retainers 156 are threaded into mounting plates 152. Retainers 156 force valve stems 158 of the tanks 54 against inlets 148 to seal the outlets (not shown) of valve stems 158. The recessed portions 144 and 146 of manifold block 142 provide protection for valve stems 158 of tanks 54. Therefore, the improved manifold assembly 140 facilitates loading and securing of the tanks 54 to the care cart 24, while protecting the valve stems 158.

The improved manifold assembly also manages the flow of gases to the ventilator 40. Separate pressure gauges 160 are provided on top wall 141 for each tank 54. A regulator 162 is provided to step down the pressure from the tanks 54 from about 2200 psi to about 50–55 psi. Providing two separate tanks 54 coupled to the same outlet 150 provides a back-up gas tank 54 and permits switch out of the tanks 54 without interrupting the supply of gas. It is understood that separate manifold assemblies 140 are provided on care cart 24 for both air and oxygen.

Regulator 162 in a first embodiment includes a threaded inlet 164 configured to be threaded into the threaded outlet aperture 150 from manifold block 142. Manifold block 142 includes a planar surface 166 of front wall 145 formed to include the outlet aperture 150 and an inlet aperture 168 for receiving the regulated gas supply from regulator 162. The high pressure outlet aperture 150 and the reduced pressure inlet aperture 168 are located on the same planar surface 166. The inlet aperture 168 is spaced apart from the outlet aperture 150 by a selected distance.

Figure 5:
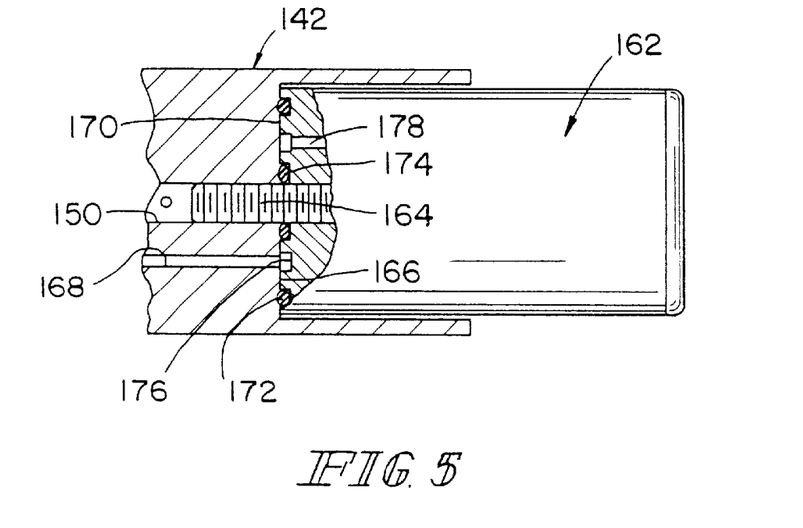
FIG. 5 is a sectional view of a manifold block and regulator when the regulator is installed into the manifold block as shown in FIG. 4.

Regulator 162 includes a regulator body including an end wall 170 having an outer annular seal 172, an inner annular seal 174 and an annular groove 176 formed between the inner and outer seals 172 and 174. Seals 172 and 174 are located within annular notches formed in end wall 170. An outlet aperture 178 of regulator 162 is formed in communication with the annular groove 176 as best shown in FIG. 5. The improved regulator 162 of the present invention facilitates alignment of the outlet 178 with the inlet aperture 168 on manifold block 142.

In prior art devices, an outlet is formed in a side wall 177 of regulator 162. One such prior art device is a model number RKX202-6092 regulator available from Flowtec Inc. located in Indianapolis, Ind. In these prior art devices, the outlet of the regulator must be rotated to a precise orientation to communicate with an inlet aperture formed in a side wall 179 of a manifold block.

As shown in FIG. 5, the high pressure supply from tanks 54 passes through the outlet aperture 150 of manifold block 142 and into regulator 162 through threaded inlet 164. Outer seal 172 and inner seal 174 engage the planar surface 166 of manifold block 142 to provide a seal around the annular groove 176. The annular groove 176 is aligned with the inlet aperture 168 of manifold block 142. The outlet aperture 178 of regulator 162 is also aligned with the annular groove 176. Therefore, the gas from regulator 162 can flow from the outlet 178 to the inlet 168 regardless of the orientation of the regulator 162 relative to the manifold block 142. In other words, aperture 178 does not have to be aligned directly over the inlet aperture 168.

Seals 172 and 174 are located on opposite sides of gas inlet aperture 168. If the seals 172 and 174 extend far enough away from the end wall 170 of regulator 162 to define a gas flow path between the end wall 170 and the planar surface 166, the annular groove 176 may be omitted.

As illustrated in FIG. 4, a cross over valve 180 is coupled to manifold block 142 on the bottom wall 143. Cross over valve 180 receives a first input from inlet aperture 168 of manifold block 142. Cross over valve 180 includes a second inlet coupler 182 configured to be coupled to a gas supply wall outlet by a hose 44 or 46. An outlet connector 184 is also coupled to cross over valve 180. The outlet connector is configured to be coupled to the critical care equipment such as the ventilator 40 by a suitable hose connection.

Figure 6:
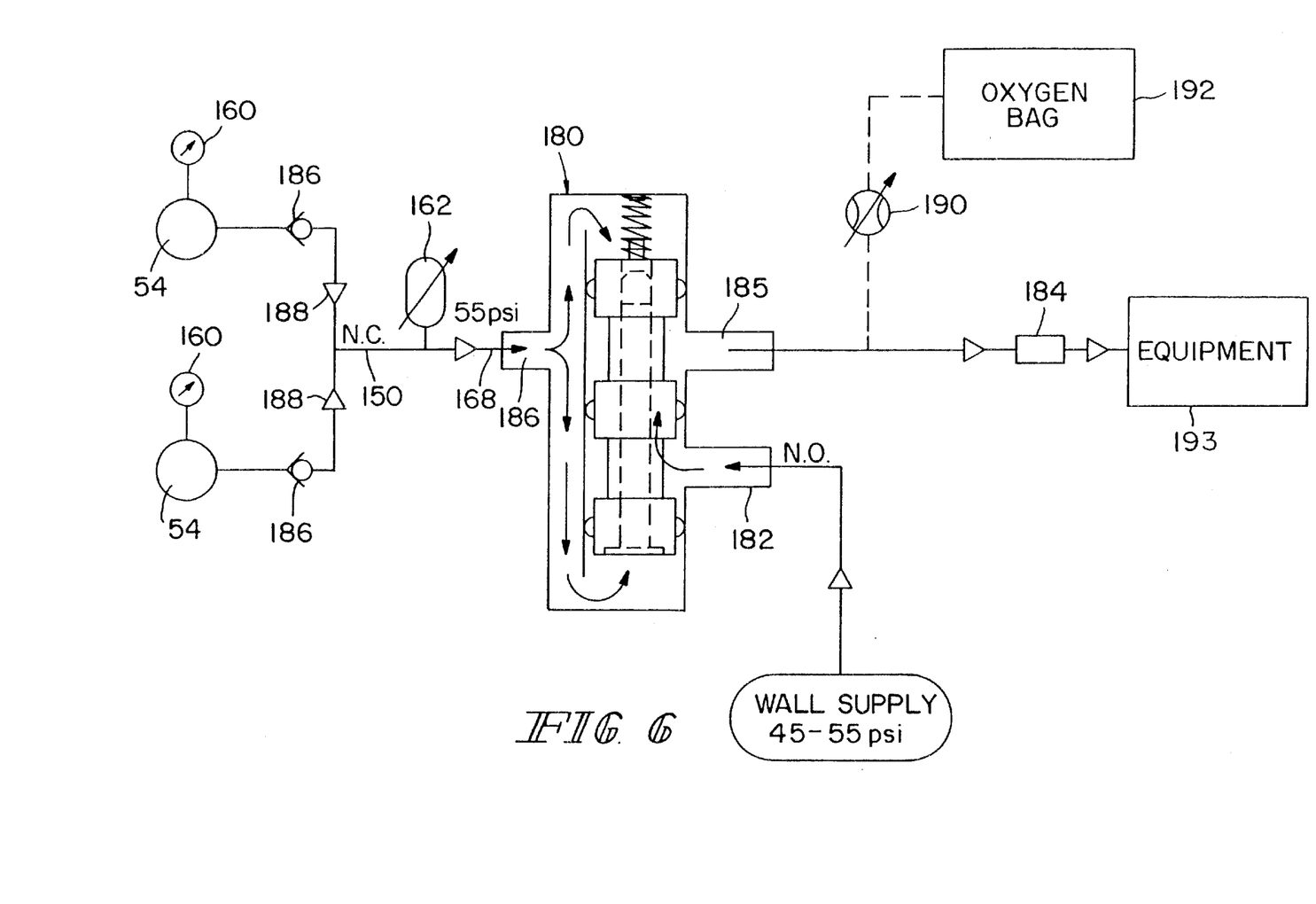
FIG. 6 is a schematic diagram of gas flow from first and second gas tanks and from a wall gas outlet through a crossover valve to the item of equipment on the care cart and to an auxiliary flow control valve.

A schematic diagram of the gas flow through the manifold assembly 140 is illustrated in FIG. 6. Check valves 186 are located within manifold block 142 and coupled to each tank 54 so that gas can flow only the direction of arrows 188. Both tanks 54 supply regulator 162 to reduce the pressure of tanks 54 from about 2200 psi to about 50–55 psi. Reduced pressure inlet aperture 168 supplies gas to a first inlet 186 of cross over valve 180. Illustratively, cross over valve 180 is a model number Y125 IN-VA1 valve available from Humphrey.

If the manifold assembly 140 is used for oxygen tanks, an adjustable flow control valve 190 mounted to the top wall 141 is coupled to an outlet 185 of cross over valve 180. An outlet from the adjustable valve 190 is coupled to an oxygen bag 192 on the cart 24. An outlet connector 184 is coupled to critical care equipment 193, such as ventilator 40.

Details of the adjustable flow control valve 190 are illustrated in FIGS. 3 and 4. Valve 190 includes a rotatable actuator 194 for adjusting the gas flow rate through an outlet connector 196. A flow rate indicator 198 is also provided. Connector 196 is coupled to an oxygen bag 192 or other equipment.

Figure 7:
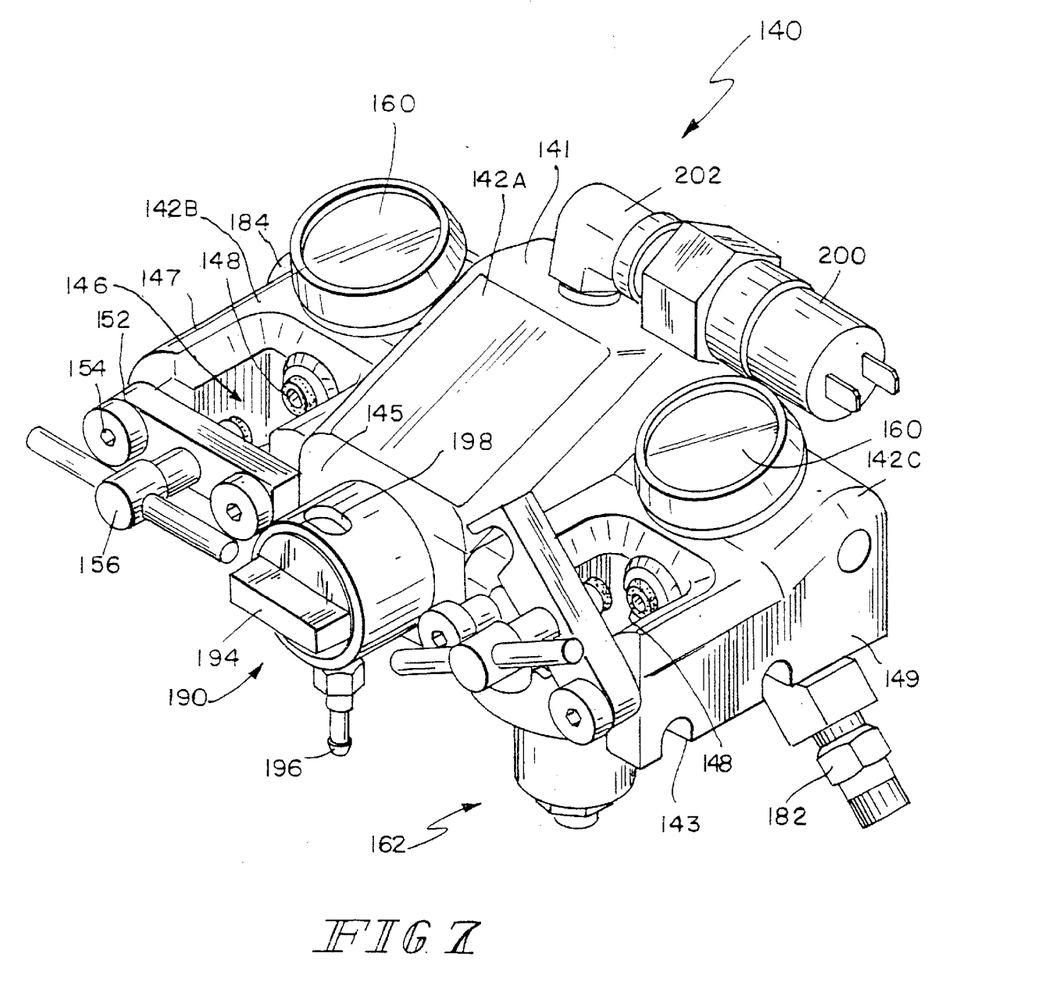
FIG. 7 is a perspective view of a oxygen manifold assembly according to the principles of the present invention.
Figures 8, 9:
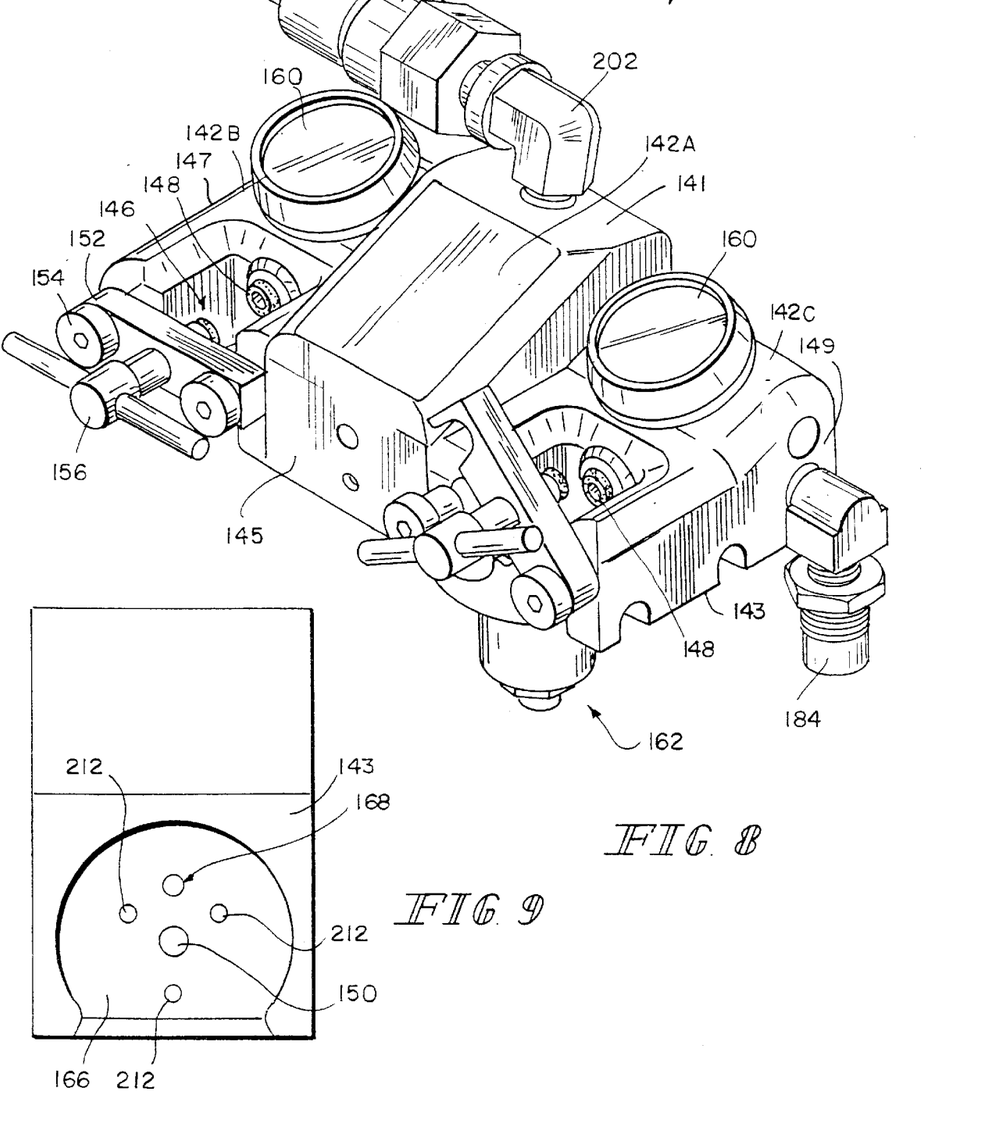
FIG. 8 is a perspective view of an air manifold assembly according to the principles of the present invention.
FIG. 9 is a bottom view of the center portion of the manifold of FIG. 7 or 8.

A second embodiment of the manifold assembly 140 and regulator 162 is illustrated in FIGS. 7–10. Those elements or components that have the same function as those in FIGS. 3–6 have the same reference number. Whereas FIG. 7 illustrates the manifold assembly 140 for oxygen and includes the oxygen flow control valve 190, FIG. 8 illustrates the manifold assembly 140 for air.

As distinguished from the first embodiment, the manifold block 142 in the second embodiment may be made up of three separate blocks, 142A being the center block, 142B being the left block and 142C being the right block. In the first embodiment, the manifold block 142 is a single element. The three piece manifold block of the second embodiment allows elements to be placed interior the manifold block 142, for example, the changeover valve 180.

Another distinction is that the adjustable valve 190 on the oxygen manifold is mounted to the front wall 145 instead of the top wall 141. The regulator 162 in the second embodiment is mounted to the bottom wall 143 instead of the front wall 145. Also, the outlet connector 184 is connected to one of the side walls, 147 in FIG. 7 and 149 in FIG. 8. The second inlet coupler 182 is still connected to the bottom wall 143.

A pressure switch 200 is connected by elbow 202 to the top wall 141 of the center manifold block 142A and is responsive to the pressure at an inlet 148 and at the same pressure as on the gauge 160. The pressure switch 200 may also be provided on the first embodiment of FIGS. 3–6.

The regulator 162 of the second embodiment mates with planar surface 166 of the bottom wall 143 as illustrated in FIG. 9. The outlet aperture 150 of the manifold block 142 is connected to the inlet 164 of the regulator 162. The planar surface 166 also includes a plurality, for example, three threaded apertures 212. Preferably, the apertures 212 and the inlet aperture 168 lie in a circle about the outlet aperture 150 in planar surface 166.

Figure 10:
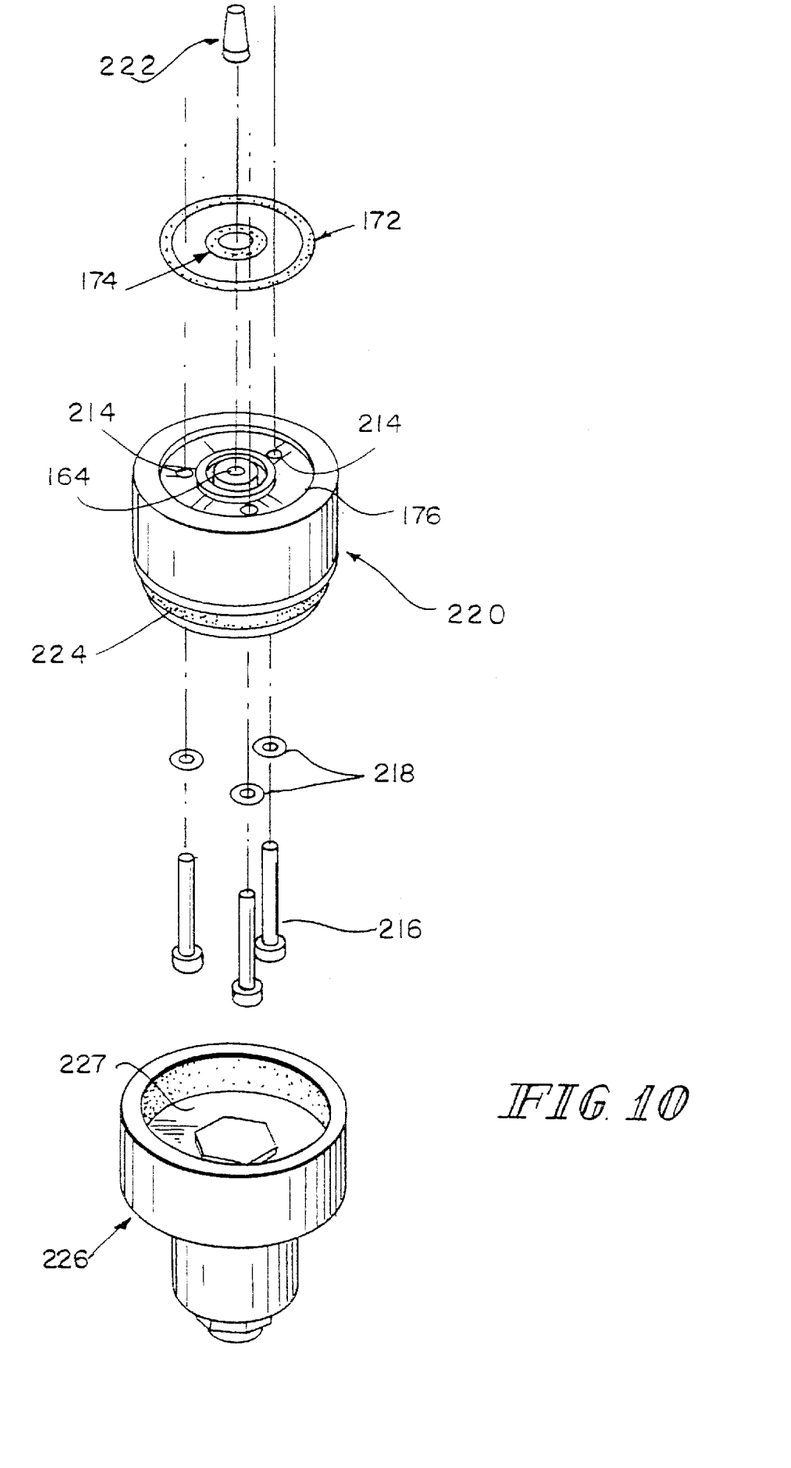
FIG. 10 is an exploded view of the regulator of FIG. 7.

As shown in FIG. 10, the end wall 170 of the regulator has an outer annular seal 172, an inner annular seal 174 and an annular groove 176 formed between the inner and outer seals 172 and 174. An inlet 164 is emcompassed by the inner seals 174. The seals 172 and 174 are located within annular notches formed in the end wall 170. An outlet aperture 178 (not shown) of the regulator 162 is formed in communication with the annular groove 176. Apertures 214 are spaced in the annular groove 176 and match with threaded apertures 212 in the planar surface 166. Fasteners 216 with lock washers 218 extend through aligned apertures 214 and 212 and mount the body 220 of the regulator 162 with the seals 172 and 174 to the manifold block 142A at surface 166.

A filter 222 is shown received in the outlet aperture 150 of the manifold 142A. A threaded surface 224 of the regulator body 220 receives a bonnet assembly 226 which covers the fasteners 216. A digraph 227 resides in the bonnet assembly 226.

It should be noted that apertures 212 in surface 166 and apertures 214 in the regulator are equally spaced about the annular groove 176. Thus, the three fasteners will always secure the regulator 162 to the block in one of three angular positions. The regulator outlet aperture 178 does not have to align with the block inlet aperture 168 because of the annular groove 176.

Figure 11:
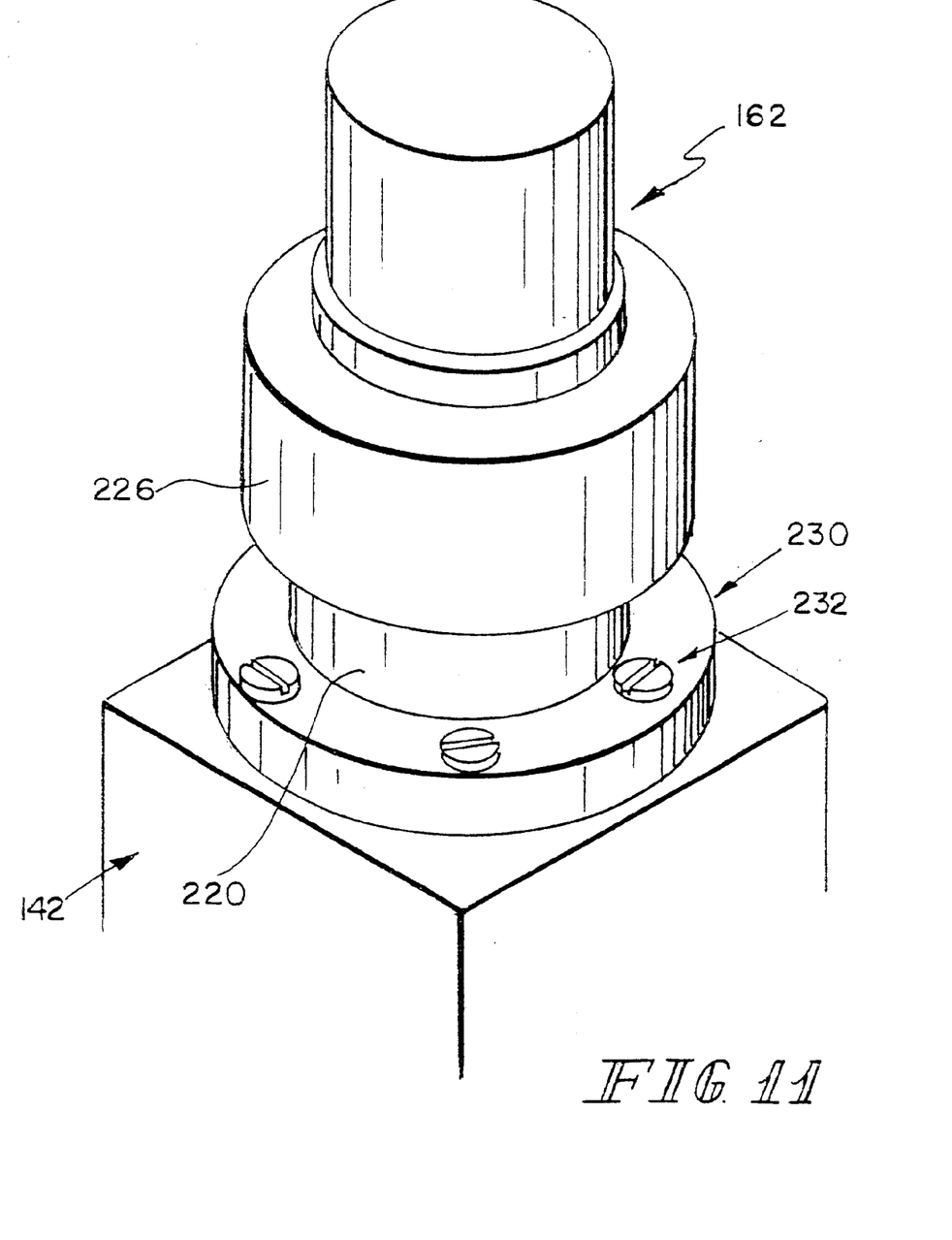
FIG. 11 is a perspective view of a third embodiment of a regulator mounted to a manifold according to the principles of the present invention.

A third embodiment for mounting the regulator 162 to the manifold block 142 is illustrated in FIG. 11. A flange 230 is provided on the regulator body 220. Fasteners 232 extend through the flange 230 and are threadably received in the manifold 142. The alignment of the fasteners 232 may be similar to the alignment of fasteners 216 of FIG. 10 or may be any alignment since they are exterior the concentric annular seals 172 and 174. The end wall 170 of the regulator 162 would include the annular groove 176 having an outlet 178 and a centered inlet 164. As distinguished from FIG. 10, the mounting fasteners are external the bonnet and therefore does not require disassembly of the bonnet 226 for mounting the regulator to the manifold.

As shown in FIG. 3, a pair of tank support platforms 201 are provided for supporting tanks 54. A spring 203 is located beneath each platform 201. Springs 203 are supported by a rigid support 204. The spring-loaded platforms 201 facilitate adjustment of the position of tanks 54 on the cart 24. When stems 158 are installed onto tanks 54, the location of an outlet on stems 158 may vary. The spring loaded platforms 201 facilitate adjustment of the tanks 54 so that an outlet of stems 158 is aligned with the inlets 148 of manifold block 142. Therefore, the tanks 154 can be loaded onto spring-loaded platforms 201 and then adjusted in the direction of double-headed arrow 207 to align the outlet of stems 158 with the inlets 148 of the manifold block 142.

In operation, tanks 54 are loaded on to the care cart 24. When it is desired the transport the patient, an actuator (not shown) is used to open a valve 208 on tanks 54 to permit gas flow from the tanks into the manifold block 142. During transport, gas is automatically supplied from tanks 54 through the manifold block 142 and cross over valve 180 to the critical care equipment 193. Regulator 162 reduces high pressure from the tanks 54 to a working pressure of the critical care equipment 193. Separate pressure gauges 60 are provided for each tank 54 to provide visual inspection of the remaining capacity within the tanks 54. Check valves 186 prevent gas flow from one tank 54 to the other tank 54.

At the transport destination, the inlet 182 of cross over valve 180 is coupled to a wall source gas supply. Gas supply from the wall sources shuttles the cross over valve 180 to stop flow of gas from the tanks 54 to the equipment 193. Gas supply from the wall outlet is immediately directed to the critical care equipment 193. Disconnecting the wall supply from the cross over valve 180 automatically allows gas flow from the tanks 54 to the critical care equipment 193, provided that the tank valves 208 are open. The oxygen flow control valve 190 delivers oxygen flow to the oxygen bag 192 when the valve 180 receives a gas supply from either the wall gas source or the tanks 54. Once the cart 24 is returned to the hospital room and the cross over valve 180 is again connected to the wall gas supply, and the valves 208 of tanks 54 are closed to conserve gas within the tanks 54.

Although the invention has been described in detail with reference to a certain preferred embodiment, variations and modifications exist within the scope and spirit of the present invention as described and defined in the following claims.

What is claimed:

1. A manifold assembly comprising:
   a manifold block having a first inlet, a first outlet, a planar surface, a second inlet formed in the planar surface, and a second outlet formed in the planar surface, the first inlet being in gas flow communication with the second outlet, the second inlet being in gas flow communication with the first outlet; and
   a regulator mounted to the manifold block at the planar surface and including a third inlet and a third outlet on a common end wall of the regulator, the third inlet being in gas flow communication with the second outlet, the third outlet being in gas flow communication with the second inlet, and one of the third inlet and third outlet being configured to encompass the other.

2. The manifold assembly according to claim 1 wherein one of the third inlet and third outlet is annular.

3. The manifold assembly of claim 2 including a first seal encompassing said one of the third inlet and third outlet, and a second seal between said one of the third inlet and third outlet and the other of the third inlet and third outlet.

4. The manifold assembly of claim 3 further including first and second annular notches formed in the end wall of the regulator, and wherein the first and second seals are O-ring seals located within said first and second annular notches.

5. The manifold assembly of claim 1 wherein the third inlet includes a threaded stem coupled to the second inlet.

6. The manifold assembly of claim 1 including at least one threaded fastener coupling the regulator to the manifold block.

7. The manifold assembly according to claim 6 wherein one of the third inlet and third outlet and the at least one fastener lie generally on a circle which encompasses the other of the third inlet and third outlet.

8. The manifold assembly of claim 7 including a first seal encompassing the said one of the third inlet and third outlet and the fastener and a second seal between said one of the third inlet and third outlet and the other of the third inlet and third outlet.

9. The manifold assembly of claim 8 further including first and second annular grooves formed in the end wall of the regulator, and wherein the first and second seals are O-ring seals located within the first and second annular grooves.

10. The manifold assembly of claim 7 wherein the regulator includes a body and a bonnet threadably mounted on the body; and the bonnet covering the fastener.

11. The manifold assembly according to claim 6 wherein the regulator includes an external flange and the at least one fastener extends through the flange to couple the regulator to the manifold block.

12. The manifold assembly of claim 1 wherein the block has top, bottom and side walls; and the planar surface is on a side wall of the block.

13. The manifold assembly of claim 12 wherein the first inlet is on the same side wall as the planar surface.

14. The manifold assembly of claim 13 including a fourth, gas inlet on the bottom wall.

15. The manifold assembly of claim 14 wherein the first outlet is on the bottom wall.

16. The manifold assembly of claim 12 wherein the first outlet is on the bottom wall.

17. The manifold assembly of claim 16 including a fourth, gas outlet on the top wall.

18. The manifold assembly of claim 1 wherein the block has top, bottom and side walls; and the planar surface is on the bottom wall.

19. The manifold assembly of claim 18 wherein the first inlet is on a side wall of the block.

20. The manifold assembly of claim 19 including a fourth, gas inlet on the bottom wall.

21. The manifold assembly of claim 19, wherein the first outlet is on another side wall.

22. The manifold assembly of claim 21 including a fourth, gas outlet on the same side wall as the first inlet.

23. The manifold assembly of claim 18 wherein the first outlet is on a side wall.

24. The manifold assembly of claim 23 including a fourth, gas outlet on another side wall.

25. A manifold assembly comprising:
a manifold block formed to include a first manifold aperture and a second manifold aperture;
a regulator coupled to the manifold block and formed to include a first regulator aperture and a second regulator aperture, the first regulator aperture being in gas flow communication with the first manifold aperture, the second regulator aperture being in gas flow communication with the second manifold aperture;
a first annular seal interposed between the manifold block and the regulator; the first annular seal having a first diameter; and
a second annular seal interposed between the manifold block and the regulator, the second annular seal having a second diameter that is larger than the first diameter, the first manifold aperture and the first regulator aperture both being positioned to lie radially inwardly of the second annular seal and radially inwardly of the first annular seal, the second manifold aperture and the second regulator aperture both being positioned to lie radially outwardly of the first annular seal and radially inwardly of the second annular seal.

26. The manifold assembly of claim 25 wherein the second annular seal is arranged in substantially concentric relation with the first annular seal.

27. The manifold assembly of claim 25 wherein the manifold block includes a planar surface, the first annular seal engages the planar surface, and the second annular seal engages the planar surface.

28. The manifold assembly of claim 27 wherein the regulator includes an end wall, the first annular seal engages the end wall, and the second annular seal engages the end wall.

29. The manifold assembly of claim 25 wherein the regulator is formed to include an annular notch in which the first annular seal is received.

30. The manifold assembly of claim 25 wherein the regulator is formed to include an annular notch in which the second annular seal is received.

31. The manifold assembly of claim 25 wherein the end wall is formed to include an annular groove positioned to lie between the first annular seal and the second annular seal, the second manifold aperture is in gas flow communication with the annular groove, and the second regulator aperture is in gas flow communication with the annular groove.

32. The manifold assembly of claim 25 wherein a gas flow path is defined in a space lying radially outwardly of the first annular seal and lying radially inwardly of the second annular seal, the second manifold aperture is in gas flow communication with the gas flow path, and the second regulator aperture is in gas flow communication with the gas flow path.

33. The manifold assembly of claim 25 wherein the regulator includes a threaded element, the first regulator aperture is formed in the threaded element, and the threaded element is threaded into the first manifold aperture to couple the regulator to the manifold block.

34. The manifold assembly of claim 33 wherein the threaded element is substantially concentric with both the first annular seal and the second annular seal.

35. The manifold assembly of claim 25 wherein the first regulator aperture and the first manifold aperture are both concentric with the first annular seal.

36. The manifold assembly of claim 25 further comprising a plurality of fasteners coupling the regulator to the manifold block.

37. The manifold assembly of claim 33 wherein each fastener of the plurality of fasteners is positioned to lie radially outwardly of the first annular seal and radially inwardly of the second annular seal.

38. The manifold assembly of claim 37 wherein each fastener of the plurality of fasteners is positioned to lie radially outwardly of both the first annular seal and the second annular seal.

39. A manifold assembly comprising:
a manifold block having a planar surface formed to include a first manifold aperture and a second manifold aperture; and
a regulator coupled to the manifold block and having an end wall that confronts the planar surface, the end wall being formed to include an annular groove, a first regulator aperture, and a second regulator aperture, the first regulator aperture being in gas flow communication with the first manifold aperture, the first manifold aperture and the first regulator aperture both being positioned to lie radially inwardly of the annular groove, the second manifold aperture and the second regulator aperture both being in gas flow communication with the annular groove.

40. The manifold assembly of claim 39 further comprising a first annular seal, the first annular seal being positioned to lie radially inwardly of the annular groove, and the first manifold aperture and the first regulator aperture being positioned to lie radially inwardly of the first annular seal.

41. The manifold assembly of claim 40 further comprising a second annular seal positioned to lie radially outwardly of the annular groove.

42. The manifold assembly of claim 42 wherein the annular groove is substantially concentric with both the first annular seal and the second annular seal.

43. The manifold assembly of claim 42 wherein the second annular seal engages the planar surface and the end wall.

44. The manifold assembly of claim 42 wherein the end wall is formed to include an annular notch in which the second annular seal is received.

45. The manifold assembly of claim 41 wherein the first annular seal engages the planar surface and the end wall.

46. The manifold assembly of claim 41 wherein the end wall is formed to include an annular notch in which the first annular seal is received.

47. The manifold assembly of claim 40 further comprising at least one fastener coupling the regulator to the manifold block.

48. The manifold assembly of claim 47 wherein the at least one fastener is positioned to lie radially outwardly of the annular groove.

49. The manifold assembly of claim 47 wherein the at least one fastener is positioned to lie radially inwardly of the annular groove.

50. The manifold assembly of claim 47 wherein at least a portion of the at least one fastener is positioned to lie in the annular groove.

* * * * *